(12) United States Patent
Thompson

(10) Patent No.: US 6,348,034 B1
(45) Date of Patent: *Feb. 19, 2002

(54) SYSTEM FOR SINGLE-PUNCTURE ENDOSCOPIC SURGERY

(75) Inventor: Robert Lee Thompson, Rogers, AK (US)

(73) Assignee: Pinotage, LLC, Fayetteville, AR (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/286,222

(22) Filed: Apr. 5, 1999

Related U.S. Application Data

(63) Continuation of application No. 08/735,013, filed on Oct. 22, 1996, now Pat. No. 5,891,013.
(60) Provisional application No. 60/011,269, filed on Feb. 7, 1996.

(51) Int. Cl.[7] .................................................. A61B 1/00
(52) U.S. Cl. ........................ 600/104; 600/109; 600/101; 600/160
(58) Field of Search ................................ 600/101, 109, 600/104, 106, 107, 121, 122, 123, 153, 179, 167, 173, 178, 188, 760; 606/1, 205–211; 604/164, 264, 19, 22, 35

(56) References Cited

U.S. PATENT DOCUMENTS

| | | | |
|---|---|---|---|
| 2,129,391 A | * | 9/1938 | Wappler ..................... 600/104 |
| 4,646,722 A | | 3/1987 | Silverstein et al. |
| 4,750,475 A | | 6/1988 | Yoshihashi |
| 4,756,309 A | * | 7/1988 | Sachse et al. ............... 600/104 |
| 4,759,348 A | | 7/1988 | Cawood |
| 4,762,120 A | | 8/1988 | Hussein |
| 4,855,838 A | | 8/1989 | Jones et al. |
| 4,867,138 A | | 9/1989 | Kubota et al. |
| 4,888,639 A | | 12/1989 | Yabe et al. |
| 4,890,159 A | | 12/1989 | Ogiu |
| 4,947,827 A | | 8/1990 | Opie et al. |
| 4,979,498 A | | 12/1990 | Oneda et al. |
| 4,989,586 A | | 2/1991 | Furukawa |
| 5,025,778 A | | 6/1991 | Silverstein et al. |
| 5,048,508 A | | 9/1991 | Storz |
| RE34,110 E | | 10/1992 | Opie et al. |
| 5,166,787 A | | 11/1992 | Irion |

(List continued on next page.)

FOREIGN PATENT DOCUMENTS

| | | |
|---|---|---|
| EP | 0 501 088 | 9/1992 |
| WO | WO 91 04703 | 4/1991 |
| WO | WO 94 10920 | 5/1994 |

OTHER PUBLICATIONS

European Search Report from European Application No., 97906506.7 dated Mar. 8, 1999.

*Primary Examiner*—Glenn K. Dawson
(74) *Attorney, Agent, or Firm*—Wolf, Greenfield & Sacks, P.C.

(57) ABSTRACT

A cannula is divided longitudinally into a camera chamber and an instrument passage. The distal end of the camera is sealed by an optically clear member. In use, a camera assembly which includes a camera sled on which are mounted a charge-coupled device camera and lights is inserted into the camera chamber and a conventional laparoscopic instrument is inserted into the patient through the instrument passage. The camera sled is isolated from the patient by the cannula, eliminating the need to sterilize the camera sled. The instrument is held in position by an attachment member which extends from the cannula. This allows the surgeon to control the position of the instrument and the camera with one hand. The cannula includes a port for connecting a source of $CO_2$ to inflate the patient's abdominal cavity and a port for connecting a conventional suction/irrigation trumpet-valve assembly.

17 Claims, 2 Drawing Sheets

U.S. PATENT DOCUMENTS

| | | |
|---|---|---|
| 5,172,225 A | 12/1992 | Takahashi |
| 5,193,525 A | 3/1993 | Silverstein et al. |
| 5,235,965 A | 8/1993 | Hirova |
| 5,243,967 A | 9/1993 | Hibino |
| 5,257,617 A | 11/1993 | Takahashi |
| 5,261,392 A | 11/1993 | Wu |
| 5,325,847 A | 7/1994 | Matsuno |
| 5,342,299 A | 8/1994 | Snoke et al. |
| 5,376,960 A | 12/1994 | Wurster |
| 5,380,291 A | 1/1995 | Kaali |
| 5,402,768 A | 4/1995 | Adair |
| 5,408,992 A | 4/1995 | Hamlin et al. |
| 5,508,735 A | 4/1996 | Mueller |
| 5,518,501 A | 5/1996 | Oneda et al. |
| 5,551,945 A | 9/1996 | Yabe et al. |
| 5,551,946 A | 9/1996 | Bullard |
| 5,554,098 A | 9/1996 | Yabe et al. |
| 5,569,254 A | 10/1996 | Carlson et al. |
| 5,609,561 A | 3/1997 | Uehara et al. |
| 5,626,595 A | 5/1997 | Sklar et al. |
| 5,643,175 A | 7/1997 | Adair |
| 5,800,344 A * | 9/1998 | Wood et al. ............ 600/188 |
| 5,891,013 A * | 4/1999 | Thompson ............... 600/104 |
| 5,928,137 A * | 7/1999 | Green .................... 600/104 |

* cited by examiner

SYSTEM FOR SINGLE-PUNCTURE ENDOSCOPIC SURGERY

This application is a continuation of application Ser. No. 08/735,013, filed Oct. 22, 1996, entitled SYSTEM FOR SINGLE-PUNCTURE ENDOSCOPIC SURGERY, now U.S. Pat. No. 5,891,013, which application claims the benefit of priority under 35 USC § 119(e) to U.S. Provisional Application No. 60/011,269, filed Feb. 7, 1996.

FIELD OF THE INVENTION

The present invention relates a system which allows endoscopic surgery to be performed using a single puncture in the patient, rather than two or more punctures required with the prior art.

SUMMARY OF THE INVENTION

The described system for performing laparoscopic surgery includes a cannula divided longitudinally into a camera chamber and an instrument passage. The distal end of the camera chamber is sealed by an optically clear cap. In use, a camera assembly is inserted into the camera chamber, a conventional laparoscopic instrument is inserted into the patient through the instrument passage, and sources of $CO_2$ and suction/irrigation are connected to ports provided on the cannula. In one embodiment of the invention, when the instrument is fully inserted into the instrument passage, the forward handle of the instrument is engaged by an attachment member which extends from the cannula. This allows the entire system (the cannula, the camera assembly, and the instrument) to be manipulated within the patient with one hand. In another embodiment of the invention, an attachment member engages the instrument adjacent to the junction of the instrument's handles.

Two camera assemblies are described. Both camera assemblies include a charge-coupled device ("CCD") camera. In one embodiment, the camera is mounted at the distal end of a sled. In another embodiment, the camera is mounted at the proximal end of the sled and a fiber optic bundle is optically connected to the camera and extends to the distal end of the sled. Both camera assemblies include two high-intensity lights mounted at the distal end of the sled. Finally, both camera assemblies include a cable which connects the camera to a display device, such as a video monitor, and the lights to a source of electrical power.

BRIEF DESCRIPTION OF THE DRAWINGS

An embodiment of the invention will be described, by way of example only, with reference to the accompanying drawings, in which.

DETAILED DESCRIPTION

Figure 1:
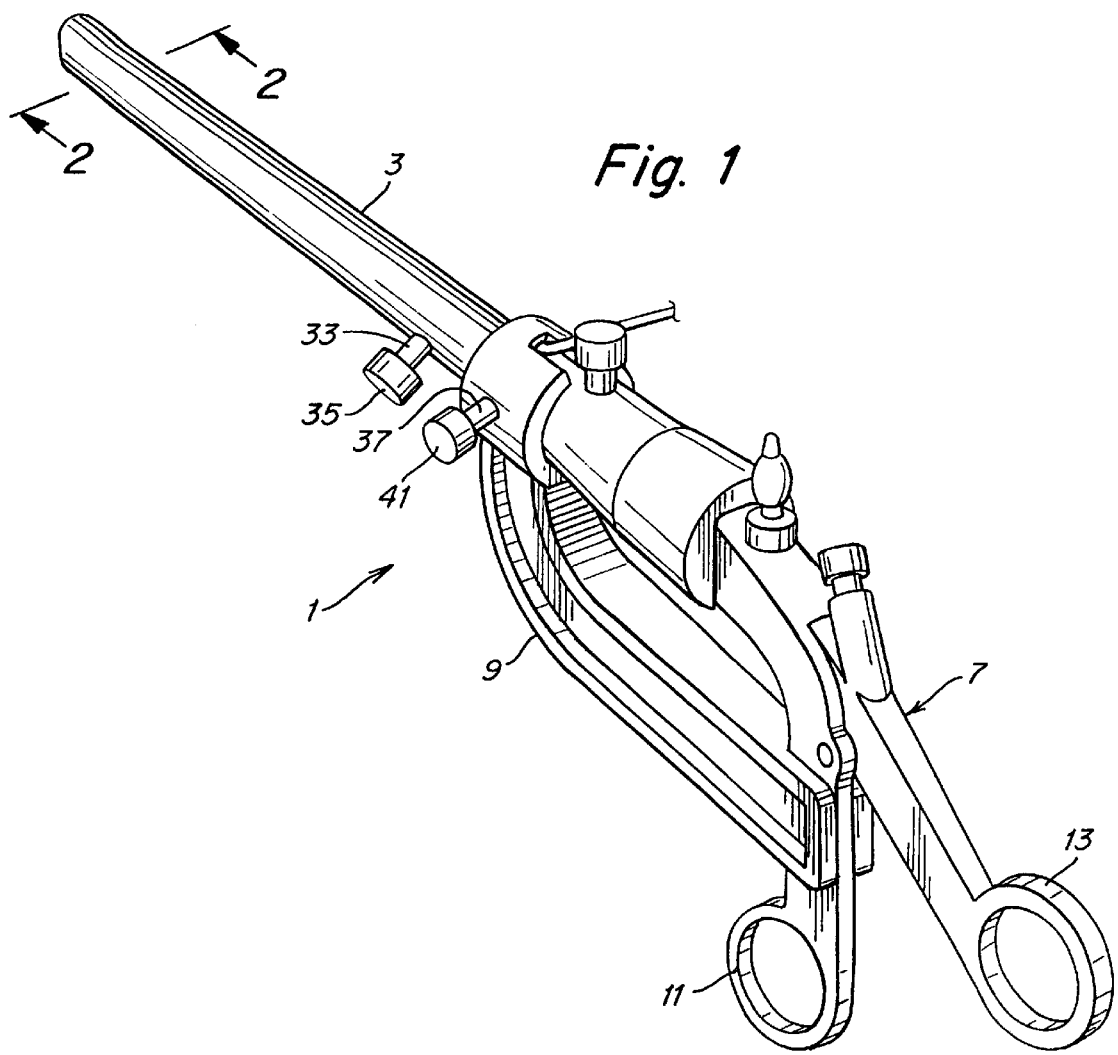
FIG. 1 is a perspective view of a system for single-puncture laparoscopic surgery embodying the invention.
Figure 2:
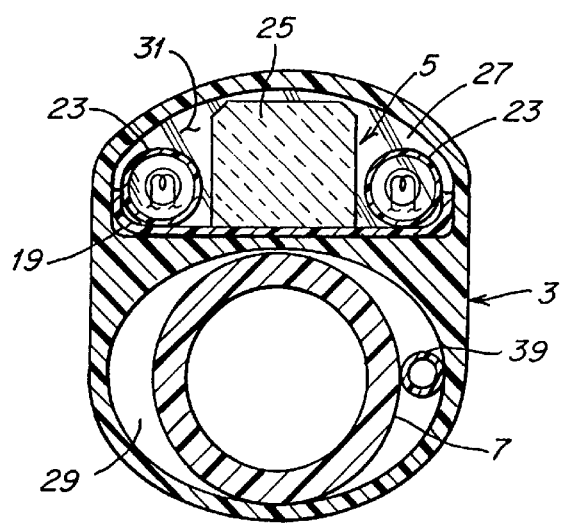
FIG. 2 is an enlarged cross-sectional view of the cannula of FIG. 1 taken through plane 2—2 in FIG. 1.
Figure 3:
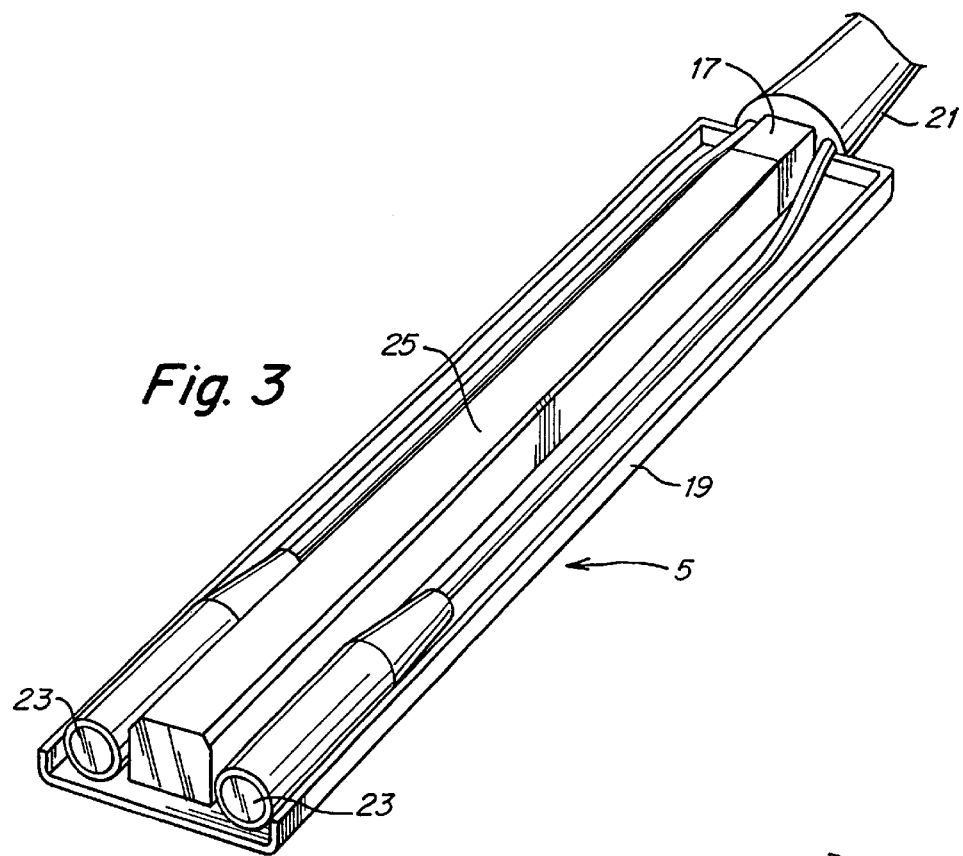
FIG. 3 is a perspective view of the camera assembly of FIG. 1.

FIGS. 1–3 illustrate a system 1 for performing laparoscopic surgery in accordance with the invention. The system comprises a cannula 3, a camera assembly 5, and a conventional laparoscopic instrument 7. The camera assembly 5 and laparoscopic instrument 7 are removably mounted in the cannula 3.

An attachment member 9 extends from the cannula 3 to engage a fixed handle 11 of the instrument 7, thereby rigidly securing the instrument 7 to the cannula 3. As a result, the system 1 can be manipulated by manipulating the laparoscopic instrument 7.

The laparoscopic instrument 7 shown in FIG. 1 is a "European style" instrument. That is, only the proximal handle 13 of the instrument 7 is movable. With an "American style" instrument both handles are movable, and the attachment member 9 is adapted to engage the instrument 7 adjacent to the junction of the handles 11, 13.

The camera assembly 5 comprises a CCD camera 17 mounted adjacent to the proximal end of an elongated sled 19. The camera 17 is connected to a display device (not shown) by a camera cable 21. The cable 21 also includes conductors which extend to and provide electrical power to a pair of high-intensity lights 23 mounted at the distal end of the sled 19. A fiber optic bundle 25 extends proximally from the distal end of the sled 19 and is optically connected to the camera 17. When the camera assembly 5 is mounted in the cannula 3, the fiber optic bundle 25 carries images from the distal end of the cannula 3 to the camera 17.

The cannula 3 is divided longitudinally into a camera chamber 27 and an instrument channel 29. An optically clear cap 31 at the distal end of the cannula 3 seals the camera chamber 27, isolating the camera assembly 5 from the patient (not shown). As a result, it is not necessary to sterilize the camera assembly 5.

A gas port 33 on the cannula 3 allows introduction of $CO_2$ gas to inflate the patient's abdominal cavity. The gas flows into the patient through the instrument channel 29. Two conventional seals (not shown) are provided near the proximal end of the instrument channel 29 to prevent escape of the gas. If the gas port 33 is not used, it is sealed with a cap 35.

A suction/irrigation port 37 on the cannula 3 is connected to a tube 39 which extends to the distal end of the instrument channel 29. In use, the suction/irrigation port 37 is connected to a conventional suction/irrigation trumpet-valve assembly (not shown). When the suction/irrigation port 37 is not used, it is sealed with a cap 41.

The cannula 3 and attachment member 9 are constructed of a suitable plastic material, such as polyurethane. They are provided in a sterilized condition and are intended to be disposed of after use.

Figure 4:
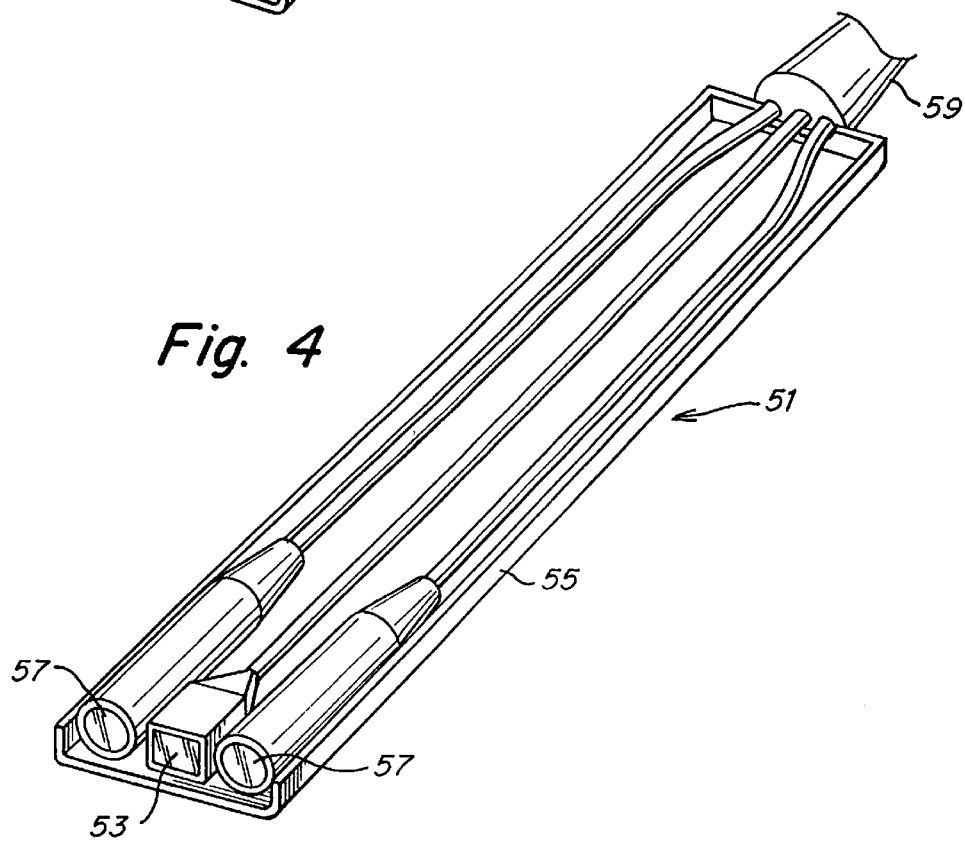
FIG. 4 is a perspective view of an alternate camera assembly.

FIG. 4 illustrates an alternate camera assembly 51. The camera assembly 51 comprises a CCD camera 53 attached to the distal end of an elongated sled 55. Also attached to the distal end of the sled 55 are two high intensity lights 57. A cable 59 connects the camera 53 to a display device (not shown) and the lights 57 to a source of electrical power.

Those skilled in the art will recognize that the invention provides a number of advantages over the prior art. Only one puncture is required, as opposed to at least two punctures with the prior art. This obviously benefits the patient, as it shortens recovery time and decreases the chance of infection.

The invention eliminates the need for an endoscope and associated light source, both of which are expensive.

The invention allows the surgeon to manipulate the camera and instrument with one hand. With the prior art, the surgeon manipulates the instrument and another person generally manipulates the endoscope/camera combination.

I claim:

1. A diagnostic system comprising:
   a cannula divided longitudinally into a first channel and a second channel;
   an optically clear cap sealingly attached adjacent to a distal end of the first channel, thereby forming a camera compartment;
   a camera adapted to be inserted in the camera compartment; and
   a light generating source adapted to be inserted in the camera compartment;
   wherein the diagnostic system is adapted for use with an instrument having an elongated shaft, the system further comprising an engagement member attached to the cannula, the engagement member being adapted to engage the instrument at a portion of the instrument that is spaced from the elongated shaft when the instrument is inserted into the second channel, so that manipulation of the portion of the instrument that is spaced from the elongated shaft can simultaneously alter positioning of the camera and the elongated shaft of the instrument.

2. A sheath for use with an instrument having an elongated shaft, the sheath comprising:
   a cannula to receive a camera and the elongated shaft of the instrument; and
   an engagement member, attached to the cannula, adapted to releasably engage a portion of the instrument that is spaced from the elongated shaft, so that manipulation of the portion of the instrument spaced from the elongated shaft can simultaneously alter positioning of the camera and the elongated shaft of the instrument, wherein the cannula is longitudinally divided into a first channel to receive the camera and a second channel to receive the elongated shaft of the instrument, and wherein the sheath further comprises an optically clear cap that seals a distal end of the first channel to prevent fluid contamination of the camera.

3. The sheath of claim 2, wherein the instrument has a pair of handles that meet at a junction, and wherein the engagement member is adapted to releasably engage the instrument adjacent the junction of the pair of handles.

4. The sheath of claim 2, wherein the instrument has a pair of handles including a non-movable handle, and wherein the engagement member is adapted to releasably engage the non-movable handle of the instrument.

5. The sheath of claim 2, wherein the instrument has a handle, and wherein the engagement member includes means for simultaneously altering positioning of the camera and the elongated shaft of the instrument in response to manipulation of the handle.

6. A diagnostic system for use with an instrument having an elongated shaft, comprising:
   a cannula;
   a viewing assembly adapted to be received in the cannula; and
   an engagement member, attached to the cannula, adapted to releasably engage a portion of the instrument that is spaced from the elongated shaft, so that manipulation of the portion of the instrument spaced from the elongated shaft can simultaneously alter positioning of the viewing assembly and the elongated shaft of the instrument, wherein the cannula is longitudinally divided into a first channel to receive the viewing assembly and a second channel to receive the elongated shaft of the instrument, and wherein the diagnostic system further comprises an optically clear cap that seals a distal end of the first channel to prevent fluid contamination of the viewing assembly.

7. The diagnostic system of claim 6, wherein the second channel is constructed and arranged to receive the elongated shaft of a rigid instrument.

8. The diagnostic system of claim 6, wherein the viewing assembly is removably mounted in the first channel, and wherein the viewing assembly includes at least one light generating source.

9. The diagnostic system of claim 8, wherein the viewing assembly further includes:
   a charge coupled device camera;
   an elongated sled having a proximal end and a distal end, the charge coupled device camera being mounted adjacent the proximal end of the sled; and
   at least one optical fiber optically coupled to the camera, the at least one optical fiber extending between the charge coupled device camera and a position adjacent the distal end of the sled;
   wherein the at least one light generating source is mounted to the sled adjacent the distal end of the sled.

10. The diagnostic system of claim 9, wherein the at least one light generating source includes two high intensity lights that are mounted to the distal end of the sled on opposite sides of the at least one optical fiber.

11. The diagnostic system of claim 8, wherein the viewing assembly further includes:
    an elongated sled having a distal end; and
    a charge coupled device camera mounted to the sled adjacent the distal end of the sled;
    wherein the at least one light generating source is mounted to the sled adjacent the distal end of the sled.

12. The diagnostic system of claim 11, wherein the at least one light generating source includes two high intensity lights that are mounted to the distal end of the sled on opposite sides of the charge coupled device camera.

13. The diagnostic system of claim 6, wherein the viewing assembly is removably mounted in the cannula and includes at least one light generating source.

14. The diagnostic system of claim 13, wherein the at least one light generating source includes at least one high intensity light bulb.

15. The diagnostic system of claim 6, wherein the instrument has a pair of handles that meet at a junction, and wherein the engagement member is adapted to releasably engage the instrument adjacent the junction of the pair of handles.

16. The diagnostic system of claim 6, wherein the instrument has a pair of handles including a non-movable handle, and wherein the engagement member is adapted to releasably engage the non-movable handle of the instrument.

17. The diagnostic system of claim 6, wherein the engagement member is rigidly attached adjacent to a proximal end of the cannula.

* * * * *